(12) United States Patent
Saathoff et al.

(10) Patent No.: US 6,271,521 B1
(45) Date of Patent: Aug. 7, 2001

(54) DEVICE AND METHOD FOR OPTICALLY DETECTING THE PRESENCE OF INGREDIENTS OF A POURABLE PRODUCT

(75) Inventors: Joerg Saathoff, Braunschwig; Eckhard Nehring, Kisdorf; Hartmut Hoyer, Kiel, all of (DE)

(73) Assignee: Bran + Luebbe GmbH, Norderstedt (DE)

( * ) Notice: Subject to any disclaimer, the term of this patent is extended or adjusted under 35 U.S.C. 154(b) by 0 days.

(21) Appl. No.: 09/194,375
(22) PCT Filed: Mar. 28, 1998
(86) PCT No.: PCT/EP98/01837
§ 371 Date: Nov. 24, 1998
§ 102(e) Date: Nov. 24, 1998
(87) PCT Pub. No.: WO98/45678
PCT Pub. Date: Oct. 15, 1998

(30) Foreign Application Priority Data

Apr. 5, 1997 (DE) .............................. 197 14 115

(51) Int. Cl.⁷ .................................................. G01N 21/35
(52) U.S. Cl. .................. 250/339.07; 250/341.1; 250/343
(58) Field of Search ......... 250/334.07, 339.12, 250/341.1, 343, 434, 435, 436, 438, 576; 356/440, 244; 73/866; 209/577

(56) References Cited

U.S. PATENT DOCUMENTS 5,212,994 * 5/1993 Von Albthan et al. ............... 73/866

FOREIGN PATENT DOCUMENTS

| 0388082 | * | 9/1990 | (EP) . |
| 2087841 | * | 11/1980 | (GB) . |
| 08285763 | * | 11/1996 | (JP) . |
| 08338804 | * | 12/1996 | (JP) . |
| WO 96/24835 | * | 8/1996 | (WO) . |

* cited by examiner

Primary Examiner—George Epps
Assistant Examiner—Richard Hanig
(74) Attorney, Agent, or Firm—Micheal J. Striker

(57) ABSTRACT

For optical determination of ingredients of a pourable product by NIR spectroscopy, to attain replicable measurement results, the device provides that the product flows in the direction of gravity; that a valve is disposed in the conduit downstream of the measurement window and a controller is embodied to move the valve to its closed position at least for the duration of measurement. The method is distinguished in that the product flows in the direction of gravity pas a measurement site; is dammed up downstream of the measurement site in such a way that the flow comes to rest at the measurement site; is dammed up in the direction of gravity past a measurement site; is dammed up downstream of the measurement site in such a way that the flow comes to rest at the measurement site; and after the measurement, the product is removed from the stagnant segment.

13 Claims, 1 Drawing Sheet

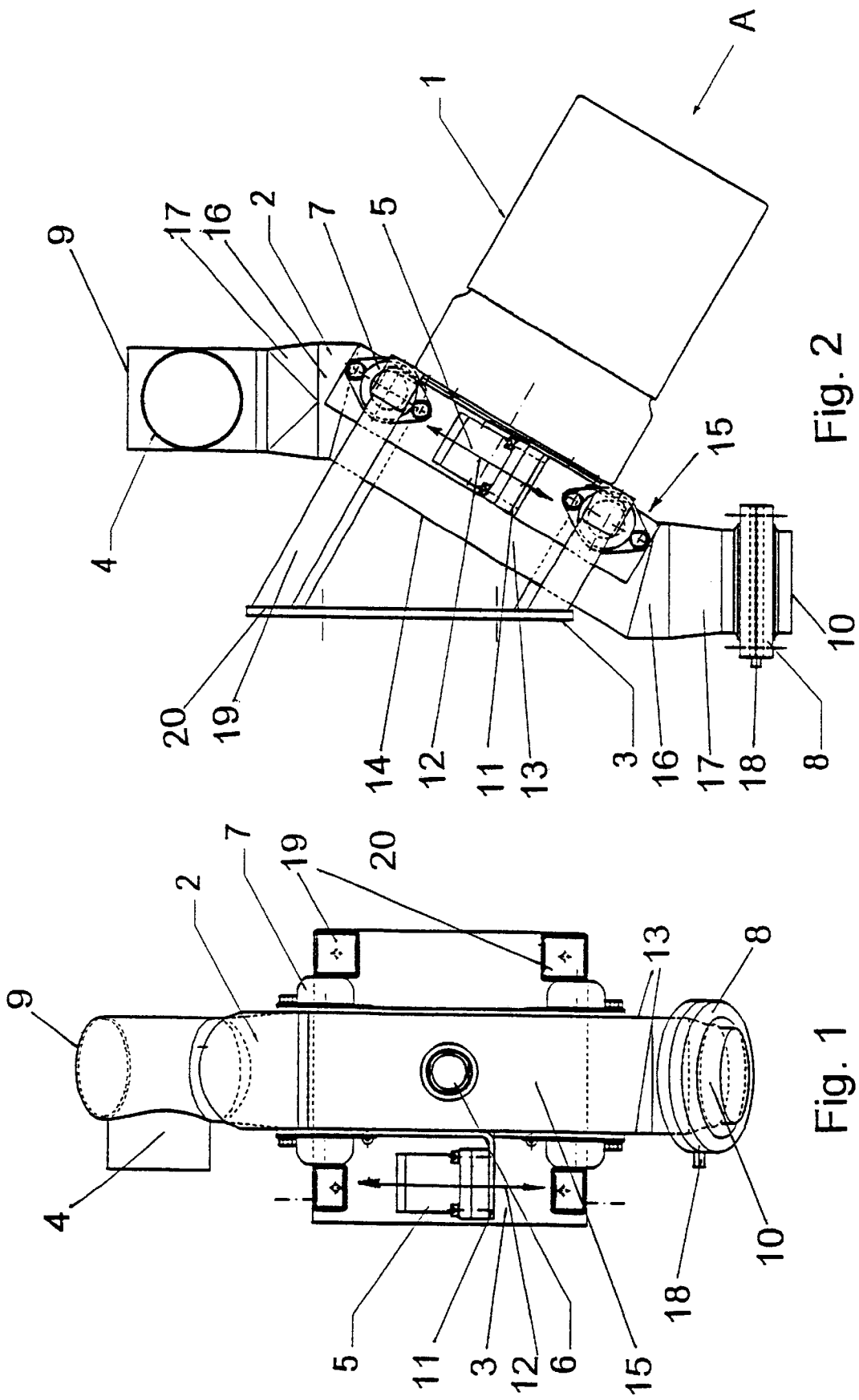

DEVICE AND METHOD FOR OPTICALLY DETECTING THE PRESENCE OF INGREDIENTS OF A POURABLE PRODUCT

BACKGROUND OF THE INVENTION

The invention relates to a device for optical determination of ingredients of a pourable product, in which the product, as a stream in a conduit, passes a measurement window, in particular for analysis by means of a spectrometer with a predetermined measurement duration for performing the analysis.

The invention also relates to a method for near-time optical determination of ingredients in the stream of a pourable product, preferably by spectroscopic processes, in particular NIR spectroscopy.

Such devices and methods are used for presentation of pourable product, also called bulk goods, for optical analysis, for instance by means of colorimetric processes but in particular also for spectroscopic optical analysis. Replicable presentation which has the least possible variance in the result for identically composed bulk products, presents problems especially for poorly flowing powdered bulk goods with very small particle size. Particular attention must therefore be dedicated to preparing the specimens. This can be assured in the laboratory by suitable manual handling of the specimens. Problems often arise, however, in near-time monitoring of continuous processes, that is, on-line, where the corrective influence of the human being is lacking. Spectroscopic monitoring of liquids is the state of the art. Although bulk goods are also flowable, nevertheless, unlike liquids, they exhibit a very widely scattered rheological behavior, depending on the existing environmental conditions. For instance, the internal friction in such pourable products varies as a consequence of humidity and temperature, particle size, relative density, particle shape, process control, and so forth. The electrical properties also play a role, since the particles stick together more strongly with a static charge.

In particular, a steady exchange of material at the measurement window is necessary so that the results of measurement will now be adulterated. Electrostatic charges can make the exchange of material still more difficult.

Compared with laboratory measurement, on-line measurement presents some additional problems, which unless they are solved make accurate measurement impossible. The product must be fed continuously to the optics, yet during the individual measurement cycles, lasting up to about 20 seconds each, the product must not be moved. Furthermore, it must be assured that the product is thoroughly mixed. Finally, the correct, replicable product consolidation has substantial influence.

In measurements, the tendency of bulk goods to partly stick to the measurement window presents very particular problems, because this additionally adulterates the result of measurement. In the prior art, such problems are solved in various ways.

To solve these problems, European Patent Disclosure EP 0 585 691 contemplates fluidizing the powder; that is, by blowing gases in, it is converted into a fluidized bed into which the measurement window of a spectroscopic analysis system plunges.

In another apparatus in accordance with International Patent Disclosure WO 95/24633, the stream of product is carried via a vibrating feed channel. The vibrating feed channel feeds the product horizontally. In the boundary walls of the vibrating feed channel, a measurement window is provided, through which the spectroscopic analysis is performed.

A measurement system of the present Applicant, known by the tradename InfraAlyzer 600, is constructed in a similar way. In it, an optical module with the measurement window is disposed above the vibrating feed channel. The vibrating feed channel serves to furnish the most constant possible layer thickness of the stream of bulk goods. Disposing the measurement window above the vibrating channel prevents soiling of the window.

Finally, British Patent GB 2 142 721 discloses an apparatus for measuring powdered material in which the material is moved past a measurement window in a conduit with the aid of a worm conveyor. During the measurement, feeding is interrupted.

A disadvantage of the known apparatuses is their relatively complicated construction, which requires major expense for apparatus and engineering. Furthermore, constant operating conditions can be assured only with difficulty.

SUMMARY OF THE INVENTION

The object of the invention is therefore to disclose another device of the type generically defined at the outset for determining ingredients of a pourable product that allows accurate measurement of various products at less effort and expense.

The generic method should furnish an operationally reliable constant mechanical quality of the specimen and thus less variance of the results of measurement.

The object in terms of the device is attained in a device of the generic type in question in that the stream at the measurement site has a flow direction with a component in the direction of gravity; a valve with an open position and a closed position is disposed downstream of the measurement window in the conduit; and a controller is provided, which is embodied to move the valve into its closed position at least for the duration of the measurement. The construction of this device is surprisingly simple and can be assembled at little effort and expense using the usual parts in such system construction.

Uniform consolidation of the product is reinforced if an overflow is disposed upstream of the measurement window. As a result, the static pressure in the bulk goods remains largely constant. A metering scales with a scales-controlled valve that interrupts the oncoming flow of further product once a predetermined fill level has been reached can thus advantageously be avoided.

In addition, in a further feature of the invention, for the sake of consolidation, it is provided that the conduit, in the region of the measurement window, is embodied as a movable container with preferably flat side walls, and a drive is provided for generating a vibrating motion of the container.

Continuous self-cleaning of the measurement window is attained in that the measurement window in the container has an angle of inclination to the horizontal that is equal to or greater than a slope gradient of the pourable product.

This self-cleaning of the measurement window is further reinforced if the container has a fall line in the vicinity of which the measurement window is disposed. In particular, the measurement window should be disposed in the projection of a fall conduit onto the horizontal plane. When the measurement container is filled, the bulk goods drop onto the window, thereby assuring the exchange of the product at the window.

The same purpose is served by the provision that the motion of the container has a directional component which differs from the direction of the normal to the measurement window face and preferably corresponds to the fall line of the measurement window face.

An explosion proof embodiment of the drive can be dispensed with, if the drive of the container is embodied as a pneumatic drive, preferably with a piston moved rectilinearly. Pistons of this kind, moved back and forth on a straight line by compressed air and whose reaction forces are intended to shake the container, are known as free-flight jolters. They have the advantage that the reaction forces, used to drive the container, act essentially only in the direction of motion of the piston. They can therefore be employed purposefully for consolidation and feeding of the product in the operating direction of the drive.

If this drive is operated such that the free-flight piston does not execute hard impacts but instead is merely reversed in its direction of motion by the air cushion, then advantageously, low-frequency vibration with especially readily replicable, mild consolidation is obtained.

In a further feature of the invention, it is provided that the spectrometer is an NIR spectrometer, in particular with a filter wheel. Such spectrometers are especially suitable in conjunction with the device of the invention, because they have relatively long durations of measurement.

During this duration of measurement, the specimen must not change. This is assured in an especially suitable way by the device according to the invention if the controller is embodied to shut off the drive during the duration of measurement.

The formation of bridges in the product in the container can be averted by providing that the controller is embodied to operate the drive as long as the valve is in its open position. As a result, the feeding of the product out of the container is also reinforced.

The object in terms of the method is attained in a method of the generic type defined above in that the product moves past a measurement site with a directional component in the direction of gravity; the stream of product is dammed up downstream of the measurement site in such a way that a stagnant segment results that allows the flow to come to rest at the measurement site, and then the ingredients are ascertained at the measurement site by measurement of a spectrum, and after that the product is removed from the stagnant segment. Surprisingly, in many cases for replicable consolidation it suffices to utilize the gravity of the pourable product itself, and as a result the method of the invention can advantageously be simply converted constructively into an apparatus without excessive effort or expense. Since gravity is not subject to any external influences, the method has an especially high degree of operational reliability, with less variance in consolidation.

A constant static pressure in the container is attained in that upstream of the measurement site, during the determination of the ingredients at the measurement site, the stream of product is interrupted or moved past, preferably by overflowing.

Further consolidation is possible if the product located in the stagnant segment is consolidated by vibration.

The outflow of the product from the stagnant segment is facilitated by providing that to remove the product from the stagnant segment, the product is loosened, preferably by means of vibration. For instance, through lateral openings through which a surge of compressed air can be introduced into the product, a bridge formed in the consolidation can easily be broken up again. Without additional expense for apparatus and engineering, however, a jolter for discharging the product can be utilized, if the product has also previously been consolidated by the jolter.

Because of the reliably replicable mechanical constancy of the specimens and because they vary only slightly over time, the method can especially be employed if the measurement is effected at certain bands of an NIR spectrum, which are determined by filtering.

The invention will be described in terms of a preferred embodiment in conjunction with a drawing, and further advantageous details can be learned from the drawing figures. Functionally identical elements are provided with the same reference numerals.

Individually, the drawings show the following:

BRIEF DESCRIPTION OF THE DRAWINGS

FIG. 1: an elevation view of the device according to the invention in the direction of the arrow A in FIG. 2 without an optical module; and FIG. 2: a view of the device of FIG. 1, but with an optical module.

DESCRIPTION OF THE PREFERRED EMBODIMENTS

The device of the invention is used for presentation of pourable product for spectroscopic measurement by an optical module 1 (FIG. 2). The device itself comprises a container 2 which is movably supported in a mount 3 by means of rubber spring elements 7. The upper end of the container is determined by an overflow 4, while the lower end of the container is formed by a valve 8. An upper end 9 and a lower tube end 10 serve the purpose of connection to a conduit, not shown in further detail, for transporting the pourable product. A vibration drive 5 is mounted solidly on the container 2 by means of a bracket 11. A piston moves in the direction of the arrows 12 in the interior of this drive 5, so that its reaction forces likewise act in the direction of the arrows 12. These reaction forces are transmitted to the container 2 via the bracket 11. As a result, the container essentially also vibrates in the direction of the arrows 12. Because of the eccentric disposition of the drive 5, however, an alternating moment is also exerted on the container 2 and impresses further motion components upon the container 2, but these components are substantially less than the component in the direction of the arrows 12.

The container 2 is square in cross section, formed by the two side walls 13 and one upper wall 14 and one lower wall 15. In the lower wall 15, a window 6 is provided, through which the optical module 1 performs the measurement. The window 6 has an inclination of about 60° from the horizontal. This angle exceeds a slope gradient of the pourable product. The term "slope gradient" is understood to mean the angle that comes to be established between the surface and the horizontal of bulk material in repose or exposed to vibration. Measuring instruments that dynamically or statically measure this angle exist.

Because the measurement window 6 is provided in the bottom wall 15 of the container, there is a constant exchange of product at the measurement window. To reinforce this effect, the measurement window is located inside the area of projection of the tube end 9 on the horizontal. The motion component oriented transversely, that is, parallel to the surface of the window, has an additional effect in exchanging product.

To allow the container to be introduced into a fall conduit for the pourable product, two angle brackets 16 and adapters 17 are provided both above and below, which in turn adapt the square cross section to the circular cross section of the adjoining tube.

For the measurement, first the valve 8 is closed by means of an adjusting drive (not shown) mounted on a shaft 8 extended to the outside. The pourable product entering at the upper tube end is dammed up by the valve 8 as a result, until it reaches the lower edge of the overflow 4. The pourable product that continues to flow in can then flow past the device through the overflow 4.

At the same time, the jolter 5 is operated. The pourable product located in the container 2 is consolidated by the motions of the container. Trapped air bubbles can escape at the top. After typically about 20 to 40 seconds, preferably 30 seconds, a consolidation of the pourable product is attained that no longer varies substantially even if jolting is continued. The jolter is then turned off, and the optical module 1 of the spectrometer can perform the measurement through the window 6.

Depending on the type of pourable product, additional consolidation by means of a jolter may also be dispensed with.

As soon as the measurement is completed, the controller opens the valve 8 again, so that the pourable product in the container can flow out. The formation of bridges and plugs in the conduit is effectively avoided by turning on the drive 5.

The product flowing in now collides in the vertical case with the obliquely placed window 6 in the wall 15. Any particles from the prior measurement sticking to it are carried away by the material flowing in after. Once the valve 8 is closed again, the product is dammed up for a further measurement. A measurement cycle as already described above thus ensues.

In most cases, the container may have a vertical axis, so that the tube ends 9 and 10 are concentric. As a result, the device of the invention can easily be installed in existing fall conduits.

A device and a method are thus created that enable uniform, replicable consolidation of bulk goods and assure optimal specimen presentation at the optical window to assure the replicability of the results of measurement in spectroscopic analysis. Various interfering physical variables are advantageously precluded from affecting the measurement.

Because only a few parts are used and especially if a flight piston jolter is selected from the drive, the device is especially robust in construction. In addition, the device can easily be integrated into the most various production processes using suitable tubular construction components. It is especially important in the context of food production that the device is also CIP/SIP-cleanable. This construction, which is suitable from a health and food standpoint, makes it possible in particular to analyze pharmaceuticals and foods spectroscopically on-line. Poorly accessible corners and dead spaces in which microorganisms could becomes established are advantageously avoided in this construction.

LIST OF REFERENCE NUMERALS

1 Optical module
2 Container
3 Mount
4 Overflow
5 Drive
6 Window
7 Rubber spring element
8 valve
9 Upper tube end
10 Lower tube end
11 Bracket
12 Directional arrows
13 Side walls
14 Top wall
15 Bottom wall
16 Angle element
17 Adapter
18 Shaft
19 Support
20 Flange plate

What is claimed is:

1. A device for optical determination of ingredients of a pourable product, in which the product, as a stream in a conduit, passes a measurement window (6), for analysis by means of a spectrometer (1) with a predetermined measurement duration for performing the analysis, wherein the stream at the measurement window (6) has a flow direction with a component in the direction of gravity; a valve (8) with an open position and a closed position is disposed downstream of the measurement window (6) in the conduit; a controller is provided, which is embodied to move the valve into its closed position at least for the duration of the measurement: the conduit, in the region of the measurement window, is embodied as a movable container (2) with side walls (13, 14, 15), and a drive (5) is provided for generating a vibrating motion of the container; the motion of the container (2) has a directional component which differs from the direction of the normal to the measurement window face.

2. The device for optical determination of ingredients of a pourable product of claim 1, wherein an overflow (4) is disposed upstream of the measurement window (6).

3. The device for optical determination of ingredients of a pourable product of claim, wherein the measurement window (6) in the container has an angle of inclination to the horizontal that is equal to or greater than a slope gradient of the pourable product.

4. The device for optical determination of ingredients of a pourable product of claim 1, wherein the container (2) has a fall line in the vicinity of which the measurement window (6) is disposed.

5. The device for optical determination of ingredients of a pourable product of claim 1, wherein, the drive (5) of the container (2) is embodied as a pneumatic drive, with a piston moved rectilinearly.

6. The device for optical determination of ingredients of a pourable product of claim 1, wherein the spectrometer (1) is an NIR spectrometer, with a filter wheel.

7. The device for optical determination of ingredients of a pourable product of claim 1, wherein the controller is embodied to shut off the drive (5) during the duration of measurement.

8. The device for optical determination of ingredients of a pourable product of claim 1, wherein the controller is embodied to operate the drive (5) as long as the valve is in its open position.

9. A device for optical determination of ingredients of a pourable product as defined in claim 1, wherein the side walls (13, 14, 15) are flat.

10. A device for optical determination of ingredients of a pourable product as defined in claim 1, wherein the directional component of the motion of the container (2) corresponds to the fall line of the measurement window face.

11. A method for near-time optical determination of ingredients in the stream of a pourable product, by spectroscopic processes, wherein the product moves past a measurement site with a directional component in the direction of gravity; the stream of product is dammed up downstream of the measurement site in such a way that a stagnant segment results that allows the flow to come to rest at the measurement site, the product is consolidated by vibration and then the ingredients are ascertained at the measurement site by measurements of a spectrum, and then the product is removed from the stagnant segment by loosening.

12. The method for near-time optical determination of ingredients in the stream of a pourable product of claim 11, wherein upstream of the measurement site, during the determination of the ingredients at the measurement site, the stream of product is interrupted or moved past.

13. The method for near-time optical determination of ingredients in the stream of a pourable product of claim 11, wherein the measurement is effected at certain bands of an NIR spectrum, which are determined by filtering.

* * * * *